United States Patent [19]
Lappas

[11] Patent Number: 5,224,932
[45] Date of Patent: Jul. 6, 1993

[54] SYSTEM FOR INTRAVENOUS ADMINISTRATION OF A PLURALITY OF MEDICAMENTS AND/OR NUTRIENTS

[75] Inventor: Dolores M. Lappas, Manhasset, N.Y.

[73] Assignee: venIVee, Inc., Yardley, Pa.

[21] Appl. No.: 557,895

[22] Filed: Jul. 25, 1990

Related U.S. Application Data

[63] Continuation-in-part of Ser. No. 249,884, Sep. 27, 1988, abandoned.

[51] Int. Cl.⁵ .............................................. A61M 5/14
[52] U.S. Cl. ...................................... 604/80; 604/173
[58] Field of Search ............... 609/258; 604/80-86, 604/56, 92, 173, 246-262, 408-410

[56] References Cited

U.S. PATENT DOCUMENTS

| | | | |
|---|---|---|---|
| 2,493,326 | 1/1950 | Trinder | 128/325 |
| 2,896,619 | 7/1959 | Bellamy, Jr. | 128/214 |
| 2,954,028 | 9/1960 | Smith | 604/80 |
| 3,495,595 | 2/1970 | Soper | 128/350 |
| 3,698,383 | 10/1972 | Baucom | 128/2 G |
| 4,072,146 | 2/1978 | Howes | 128/2.05 D |
| 4,150,673 | 4/1979 | Watt | 128/272 |
| 4,298,000 | 11/1981 | Thill et al. | 604/236 X |
| 4,439,193 | 3/1984 | Larkin | 604/411 |
| 4,441,373 | 4/1984 | White | 73/864.02 |
| 4,460,366 | 7/1984 | Shinno | 604/408 |
| 4,557,959 | 12/1985 | Koehlein et al. | 428/36 |
| 4,583,979 | 4/1986 | Palti | 604/256 |
| 4,597,754 | 7/1986 | Thill et al. | 604/154 |
| 4,608,997 | 9/1986 | Conway | 128/763 |
| 4,619,640 | 10/1986 | Potolsky et al. | 604/7 |
| 4,654,026 | 3/1987 | Underwood | 604/350 |
| 4,795,429 | 1/1989 | Feldstein | 604/80 |
| 4,892,524 | 1/1990 | Smith | 604/246 |
| 4,966,585 | 10/1990 | Gangemi | 604/131 |

Primary Examiner—C. Fred Rosenbaum
Assistant Examiner—Mark O. Polutta
Attorney, Agent, or Firm—Panitch, Schwarze Jacobs & Nadel

[57] ABSTRACT

A system for the intravenous administration of a plurality of medicaments and/or nutrients contained in respective liquid containers includes a plurality of liquid intravenous administration sets, each administration set defining a flow path from a point of entry adapted to be fluidly connected to a respective liquid container to a point of exit adapted to be fluidly connected to a vasopuncture device, the flow path being bounded over a portion of its length by a flexible intravenous tube, and a plurality of indicia, each designating a respective one of the liquid reservoirs containing one of the medicaments and/or nutrients and associated with a respective one of the administration sets defining a flow path from that liquid reservoir designated by the indicia. In a preferred embodiment, the plurality of indicia comprise respective colors, each color designating a respective one of the liquid containers containing one of the medicaments and/or nutrients.

6 Claims, 2 Drawing Sheets

SYSTEM FOR INTRAVENOUS ADMINISTRATION OF A PLURALITY OF MEDICAMENTS AND/OR NUTRIENTS

CROSS-REFERENCE TO RELATED APPLICATION

This application is a continuation-in-part of copending U.S. patent application Ser. No. 249,884, filed on Sep. 27, 1988, now abandoned.

FIELD OF INVENTION

This invention relates generally to intravenous administration of medicaments and/or nutrients and, more particularly, to systems for intravenous administration of a plurality of medicaments and/or nutrients contained in respective liquid containers.

BACKGROUND OF THE INVENTION

The intravenous administration of liquids or, more particularly, medicaments and/or nutrients (collectively referred to below as medicaments) is commonplace. A medicament is so administered using an administration set including means defining a flow path having an upstream or entry end adapted to be fluidly connected to a liquid container or reservoir, e.g. a bottle or bag, containing the medicament and a downstream or exit end adapted to be fluidly connected to a vasopuncture device which is inserted into the patient's blood vessel, e.g. artery. The flow path is defined over a major portion of its length by a flexible intravenous tube formed of light-transmitting, e.g. clear, plastic material.

It is becoming more common to run a plurality of "I.V. lines" to a patient, i.e. to simultaneously intravenously administer a plurality of medicaments from respective liquid containers through respective flow paths defined by a corresponding plurality of administration sets. This can be accomplished without difficulty when only two or even three lines are running.

It is not uncommon today for as many as six to nine different I.V. lines to simultaneously run through respective administration sets to a single patient. However, problems are often encountered in such cases, especially where the exit ends of the flow paths of the administration sets are fluidly connected to vasopuncture devices located proximate to each other, such as in the blood vessels of the arms, neck and head. In particular, the flexible intravenous tubes of the administration sets tend to become tangled and interwoven with each other as the patient moves or is moved by hospital personnel, due to the "memory" of the plastic material from which the tubes are made. The intravenous tubes generally tend to bow or spiral during use in an attempt to return to the curled form in which they were packaged. The tangled tubes must be simply and safely identified without the aid of additional equipment (e.g., separators).

The tangling of intravenous tubes becomes a significant problem, for example, when it is necessary during a surgical procedure to inject another drug as quickly as possible through an intermediate coupling provided in an existing I.V. line. Such situations occur for example, when a patient to whom a plurality of I.V. lines are running goes into shock and it is not possible to find another blood vessel into which to inject another drug. In such a case, it is the practice to inject the drug into the line or flexible flow path through which a benign medicament is already being administered, i.e. to "piggyback" an additional I.V. line with an existing line. However, it is not always an easy matter to distinguish one line from another in the short time available in emergency situations, such as during anaesthesia or during emergency surgical procedures. Catastrophic results may occur where a drug is inadvertently injected into an I.V. line through which a medicament is already flowing which is not compatible with the injected or "piggy-backed" drug. For example, if heparin or protamine is inadvertently injected into a line through which lidocane is already flowing, a flakey precipitate forms in the mixture which should not be injected into the patient's blood vessels.

It is seen from the foregoing that it is desirable to provide a system for the intravenous administration of a plurality of medicaments through a plurality of administration sets wherein the particular medicament flowing through each intravenous tube or line can be readily and reliably identified.

Conventional attempts to administer a plurality of medicaments through a plurality of administration sets wherein the particular medicament flowing through each intravenous tube or line can be readily and reliably identified, include the use of a plurality of administration sets wherein each intravenous tube or line for each administration set includes indicia disposed at intervals along the length of the tube. Typically, the indicia is printed on the tubes at intervals of about six inches and is printed three times at each location along the tube, around its circumference. In other conventional administration sets the indicia is printed once at each location in a spiralling pattern along the tube.

In the conventional administration sets, the I.V. tubing is constructed of clear plastic, so that the color of the fluid flowing therethrough may be easily identified. The type of indicia which is printed on the tubes includes letters, bands of color or other symbols.

However, the conventional intravenous administration sets have several drawbacks. First, the conventional systems require a three-step manufacturing process. The clear plastic tubing is first extruded and then the indicia is applied to the tubing. The indicia is then sealed to the tubing. Secondly, as mentioned above, aside from where the indicia is printed along the tubing, the I.V. tubing is constructed of clear plastic. As such, if it is necessary to quickly administer a light sensitive medicament, such as ampicillin, the I.V. tubing must first be covered with a light shielding material, such as aluminum foil. This seriously inhibits the quick administration of the medicament.

Thus, a need has arisen in the intravenous administration field for an administration set wherein the particular medicament flowing through each intravenous tube can be readily and reliably identified, is easily manufactured and readily administers light sensitive medicaments.

The present invention provides a system for the intravenous administration of a plurality of different liquids to a patient. The system includes a plurality of flexible single-walled tubes which are fabricated of a polymeric material wherein the material used to form each tube has a different coloring agent from the material used to form the other tubes such that each of the tubes is of a different translucent color throughout its entire length. Since the tubes are translucent throughout their entire length, light sensitive medicaments can be administered by the system without providing further shielding of light. Moreover, because the tubes are constructed of a polymeric material having a coloring agent, the manufacturing process is relatively simple, thereby reducing the overall cost of the administrative system. Consequently, use of the present invention results in a safer and more efficient medication delivery system without further increasing the cost of the administration set.

SUMMARY OF THE INVENTION

It is an object of the present invention to provide a new and improved apparatus for intravenous administration of a plurality of medicaments contained in respective liquid containers.

Another object of the present invention is to provide a new and improved apparatus for intravenous administration of a plurality of medicaments contained in respective liquid containers through a plurality of intravenous administration sets wherein the particular medicament flowing through an intravenous tube of an administration set can be quickly and reliably identified.

Still another object of the present invention is to provide a new and improved apparatus for intravenous administration of a plurality of medicaments contained in respective liquid containers through a plurality of intravenous administration sets and wherein another I.V. line for administering another drug can be readily and safely "piggybacked" with an intravenous tube of an existing administration set.

Briefly, in accordance with the present invention, these and other objects are obtained by providing a system for the intravenous administration of a plurality of medicaments contained in respective liquid containers, comprising a plurality of liquid intravenous administration sets, each administration set including means defining a flow path from a point of entry adapted to be fluidly connected to a respective liquid container to a point of exit adapted to be fluidly connected to a vasopuncture device, the flow path being bounded over a portion of its length by a flexible intravenous tube, and a plurality of indicia means, each respective indicia means designating a respective one of the liquid containers containing one of said medicaments and being associated with a respective one of the administration sets defining a flow path from that one of the liquid containers.

In accordance with a preferred embodiment of the invention, the plurality of indicia means comprise a plurality of respective colors, each color designating a respective one of the liquid containers containing one of the medicaments and being associated with a respective one of the administration sets defining a flow path from that one of the liquid containers.

An intravenous tube of each administration set is formed of a light-transmitting translucent plastic material and in one embodiment has a respective color comprising a respective indicia means associated with the intravenous administration set.

Each of the administration sets may include, in addition to the flexible intravenous tube, at least one injection coupling means for adding or "piggybacking" additional medicaments into the flow path between the points of entry and exit therefrom, entry means for fluidly connecting the point of entry of the flow path to a respective container, valve means disposed along the flow path for adjusting the rate of flow of liquid therethrough, and/or exit means for fluidly connecting the point of exit of the flow path to a respective vasopuncture device. One or more of the injection coupling means, entry connecting means, valve means, and/or exit connecting means may have indicia means associated therewith.

Briefly stated, the present invention comprises a system for the intravenous administration of at least two different liquids to a patient. The system comprises a first flexible single-walled tube having a first end, a second end and an interior area for administering a first liquid to a patient. The first tube is fabricated of a polymeric material having a coloring agent such that the first tube is of a first color throughout its entirety. The second end of the first tube receives insertion means for placing the tube in fluid communication with the patient. A first container is provided for storing the first liquid in an interior area thereof. The first container is fabricated of a polymeric material having a coloring agent such that the first container is of the first color through its entirety. The first end of the first tube is in fluid communication with the interior area of the first container. A second flexible single-walled tube has first end, a second end and an interior area for administering a second liquid to a patient. The second tube is fabricated of a polymeric material having a coloring agent such that the second tube is of a second color throughout its entirety. The second end of the second tube receives insertion means for placing the second tube in fluid communication with the patient. A second container is provided for storing the second liquid in an interior area thereof. The second container is fabricated of a polymeric material having a coloring agent such that the second container is of the second color throughout its entirety. The first end of the second tube is in fluid communication with the interior area of the second container. As such, the first and second tubes and the first and second liquids within the first and second tubes can be readily identified by the color of the tubes and containers.

BRIEF DESCRIPTION OF THE DRAWINGS

The foregoing summary, as well as the following detailed description, is better understood when read in conjunction with the appended drawings. For the purpose of illustrating the invention, embodiments which are presently preferred are shown in the drawings. It is understood, however, that this invention is not limited to the precise arrangements and instrumentality shown. In the drawings.

DESCRIPTION OF THE PREFERRED EMBODIMENT

Figure 1:
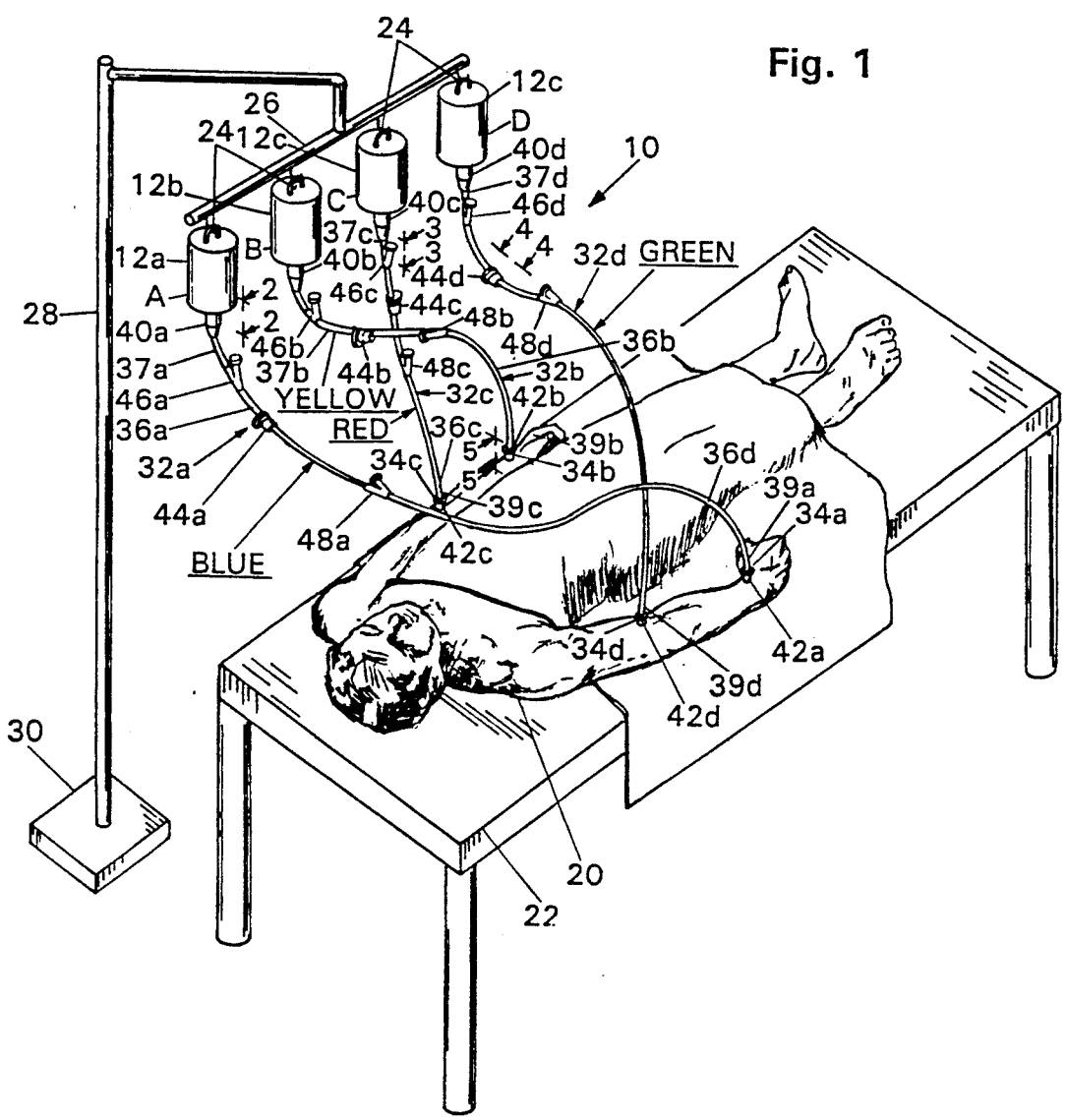
FIG. 1 is a perspective view of a system for intravenous administration of a plurality of medicaments in accordance with the present invention illustrated in use with a patient.

Certain terminology is used in the following description for convenience only and is not limiting. The words "right", "left", "lower" and "upper" designate directions in the drawings to which reference is made. The words "inwardly" and "outwardly" refer to directions toward and away from, respectively, the geometric center of the administration system and designated parts thereof. The terminology includes the words above specifically mentioned, derivatives thereof and words of similar import.

Referring now to the drawings wherein like reference characters designate identical or corresponding parts throughout the several views, and more particularly to FIG. 1, a system in accordance with the invention, generally designated 10, for intravenous administration of four different medicaments A, B, C, D contained in respective fluid reservoirs or containers 12a, 12b, 12c, 12d to a patient 20 located on an operating table 22 is illustrated. The bottles 12a-12d are suspended from a hanger bar 26 by hooks 24. Hanger bar 26 is supported on a stand 28 mounted on a base 30.

System 10 comprises four intravenous administrations sets 32a, 32b, 32c, 32d, each including means defining a flow path from an upstream point of entry coupled to a respective reservoir of medicament A-D in a respective bottle or container 12a-12d to a downstream point of exit coupled to a respective vasopuncture device 34a, 34b, 34c, 34d. Each flow path is bounded over a major portion of its length by a flexible, single-walled tube 36a, 36b, 36c, 36d. Each tube 36a, 36b, 36c, 36d includes a first end 37a, 37b, 37c, 37d, a second end 39a, 39b, 39c, 39d and an interior area 41a, 41b, 41c, 41d for administering a liquid or medicament to the patient 20. As seen in FIG. 1 the various flexible intravenous tubes 36a-36d have a tendency to bow or curve and accordingly, become tangled or interwoven with each other, especially when the vasopuncture devices are located in proximity with each other, such as in the example illustrated in FIG. 1.

It is understood by those skilled in the art that the present invention is not limited to any particular number of administration sets 32. That is, the administration system 10 can be comprised of two administration sets, nine administration sets or any number of administration sets without departing from the spirit or scope of the invention.

In order to quickly and reliably identify a particular medicament flowing through a particular intravenous tube 36, each of the tubes is formed of a light-transmitting plastic material having a particular color, each color designating a particular one of the containers 12a-12d containing one of the medicaments A-D. In the present embodiment, it is preferred that each of the tubes 36 be fabricated of a polymeric material, such as polyethylene, having a coloring agent such that each tube is of a different color throughout its entirety. In the present embodiment, it is preferred that the coloring agent be a diestuff (pigment). However, it is understood by those skilled in the art, that the present invention is not limited to any particular type of coloring agent.

Similarly, it is preferred that each of the containers 12 be fabricated of a material selected from the group consisting of a polymeric or ceramic material, such as polyethylene or glass, respectively, having a different coloring agent than the coloring agent of the other respective containers 12 such that each of the containers is of a different translucent color throughout its entirety, but is identical to the color of its associated tube 36.

It is understood by those skilled in the art, that the tubes 36 can be formed of any polymeric material and that the containers 12 can be formed of any polymeric or ceramic material. For instance, the containers 12 could be constructed of plexiglas without departing from the spirit and scope of the invention.

Consistent with standard dictionary usage the term "light transmitting plastic" includes clear, transparent and translucent plastic. For example, Webster's 9th Collegiate Dictionary states that "clear" implies "absence of cloudiness, haziness or muddiness", "transparent" implies "being so clear that objects can be seen distinctly" and "translucent" implies "the passage of light but not a clear view of what lies beyond." Similarly, The American Heritage Dictionary states that "translucent" implies the transmission of light "but causing sufficient diffusion to eliminate perception of distinct images." Thus, an object that is translucent is not transparent. The light transmitting plastic material may be of any color without departing from the spirit and scope of the invention so long as the light-transmitting plastic material is of the same color in each administration set.

In the present embodiment, it is preferred that the intravenous tubes 36a, 36b, 36c and 36d be formed by a standard injection molding or extrusion process. Preferably, the coloring agent is added directly to the material to be extruded or injected before the material is injected or extruded. However, it is understood by those skilled in the art that the intravenous tubes 36a, 36b, 36c and 36d can be formed by other conventional manufacturing methods without departing from the spirit and scope of the invention. For instance, the tubes 36 could be constructed of a clear plastic material and then dyed or painted to achieve the different colors thereof.

In the present embodiment, it is preferred that the amount of coloring agent in the polymeric material of the tubes 36 be sufficient to effectively diffuse light passing through the wall of the tubes 36 and into the interior area thereof to maintain effective administration of a light sensitive liquid or medicament. Similarly, the amount of coloring agent in the containers 12 is sufficient to effectively diffuse light passing into the interior area thereof to maintain effective administration of light sensitive liquids or medicaments (e.g., nitroprusside). Further, examples of such light sensitive liquid or medicaments include inter alia, anaesthetics, antibiotics, such as, erythromycin ethylsuccinate; erthromycin stearate; ampicillin; ampicillin trihydrate; penicillin P potassium; and penicillin V potassium and vitamins, such as, A, B2, B6, C, etc.

In the present embodiment, the blue color of intravenous tube 36a designates medicament A contained in bottle 12a, the yellow color of tube 36b designates medicament B contained in bottle 12b, the red color of tube 36c designates medicament C contained in bottle 12c, and the green color of tube 36d designates medicament D contained in bottle 12d. The different colors thus comprise a plurality of indicia means, each one of which designates a particular one of the liquid containers 12 containing a particular one of the medicaments. Each indicia means is associated with a respective one of the administration sets 32a-32d which defines a flow path from the particular liquid container 12 designated by that indicia means.

It is understood by those skilled in the art that the present invention is not limited to each intravenous tube 36a-36d being of a single color throughout its entirety but that the intravenous tubes may possess an uncolored portion, or may possess more than one indicia. Similarly, one of the plurality of intravenous tubes or administration sets may entirely or partially be colorless.

Each administration set 32 includes an entry adaptor 40a, 40b, 40c, 40d at the upstream end of the flexible intravenous tube 36a-36d for fluidly connecting the intravenous tube to a particular bottle 12a-12d, a valve means or flow regulating clamp 44a, 44b, 44c, 44d disposed along the length of the intravenous tube 36a-36d for adjusting the rate of flow of liquid medicament therethrough, and upper and lower injection couplers 46a-46d; 48a-48d provided between the entry and exit adapters comprising ports through which additional medicaments can be administered through the intravenous tube.

The second end of each tube 36 receives insertion means for placing each tube 36 in fluid communication with the patient. In the present embodiment, it is preferred that the insertion means comprise an exit adapter 42a, 42b, 42c, 42d, as is understood by those skilled in the art. Preferably, the exit adapter 42a, 42b, 42c, 42d fluidly connects the intravenous tube to a particular vasopuncture device 34a-34d. However, it is understood by those skilled in the art, that insertion means can comprise any structure or method for placing the tube 36 in fluid communication with the patient.

Figure 2:
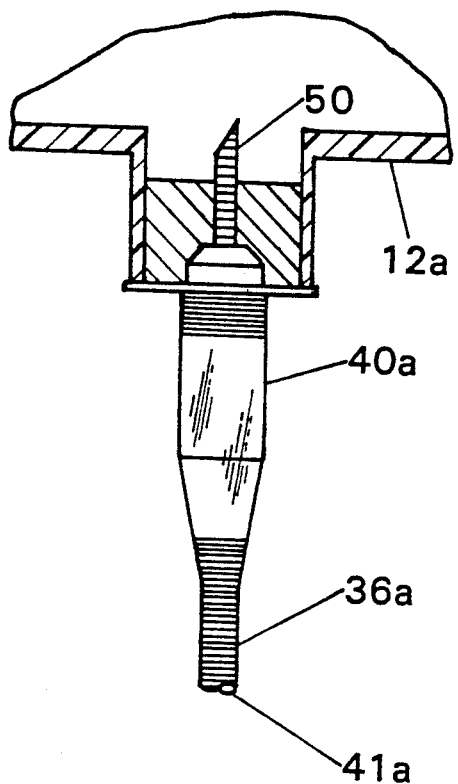
FIG. 2 is an elevational view partially in cross section taken in the direction of line 2—2 of FIG. 1 illustrating entry connecting means of the system.
Figure 3:
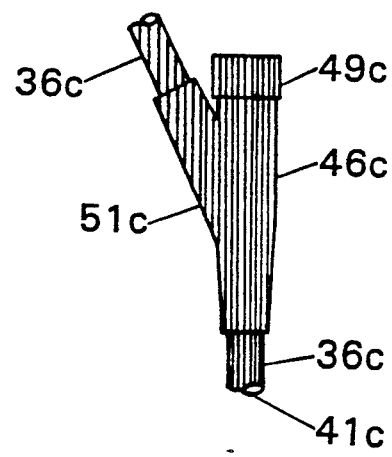
FIG. 3 is an elevational view taken in the direction of line 3—3 of FIG. 1 illustrating injection coupling means of the system.
Figure 4:
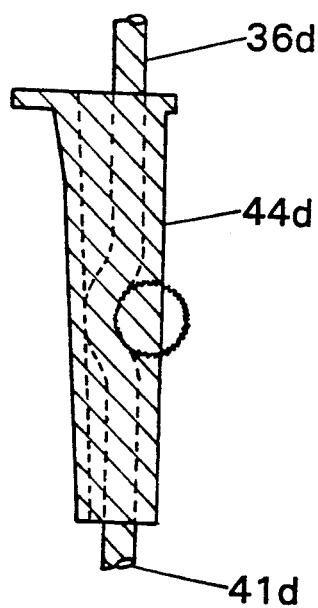
FIG. 4 is an elevational view taken in the direction of line 4—4 of FIG. 1 illustrating valve means of the system.
Figure 5:
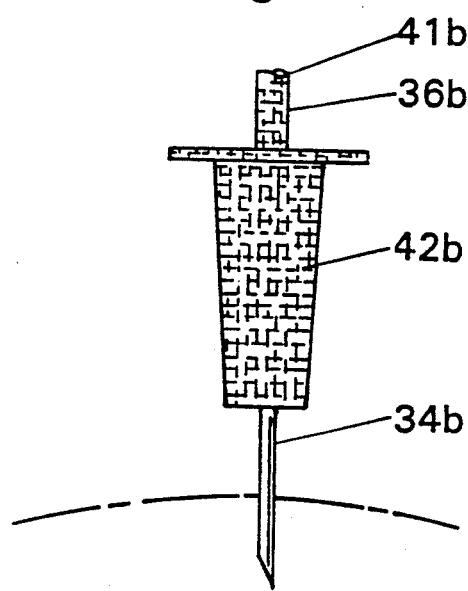
FIG. 5 is an elevational view taken in the direction of line 5—5 of FIG. 1 illustrating insertion means of the system.

In accordance with the invention, a respective one of the colors comprising the indicia means associated with a particular administration set may be applied to one or more of the entry adaptors 40, the exit adaptors 42, the valves 44 and the injection couplers 46, 48, associated with that administration set, either in addition to or in lieu of applying that color to the intravenous tube 36. Thus, the entry adaptor 40a of administration set 32a may have the color blue associated with it (FIG. 2), the exit adaptor 42b of the administration set 32b may have the color yellow associated with it (FIG. 5), the injection coupler 46c of administration set 32c may have the color red associated with it (FIG. 3) and the valve means 44d of administration set 32d may have the color green associated with it (FIG. 4).

Thus, each of the elements or hardware comprising the administration set may be provided, either alone or in combination with other elements of that administration set, with a particular one of the indicia means associated with the particular bottle 12 to which the flexible tube is coupled. It is understood by those skilled in the art, that the entry adaptors 40, the exit adaptors 42, the valves 44 and other associated hardware of the administration set may be of different contrasting color, without departing from the spirit and scope of the invention.

It is particularly advantageous to provide the indicia means on the injection couplers 46 and 48 so that the particular medicament flowing through the flow path defined by a particular administration set can be readily ascertained when it is desired to "piggyback" or inject another drug or medicament into an existing intravenous tube 36 through the couplers. As shown in FIG. 3, the injection couplers preferably include an insertion portion 49c for receiving fluid from a different administration set. The insertion portion 49c is preferably of the same color as the tube of a different administration set to thereby facilitate piggybacking another liquid. Of course, the flow through portion 51c of the injection coupler 46c is preferably of the same color as the tube 36c.

It is of course possible to also associate respective indicia means with the bottles 12 containing the respective medicaments. However, this may not be necessary in the case where respective indicia means are provided on the entry adaptors 40 which are located adjacent to each of the respective bottles. Indeed, referring to FIG. 2, each of the entry adaptors 40 may include a hollow spike 50 which extends into the bottle when the administration set is coupled thereto. This spike is generally visible within the bottle after connection and if provided with indicia means as shown will provide ready identification of the particular medicament contained therein.

It will be understood that when color indicia are used, the colors may be applied to the respective administration sets in a manner other than as described above in connection with the illustrated embodiment. For example, color indicia may be applied to each administration set by applying adhesive tape of an appropriate color to a portion or all of the intravenous tube of each administration set. More typically, and as indicated above, however, color will form an integral part of the extruded or injection molded tube. Moreover, it will be understood that indicia means other than colors may be utilized in accordance with the invention. For example, numbers, letters, etc. may be utilized as indicia means in accordance with the invention.

While it is understood that the present invention is not limited to any particular polymeric material, ceramic material or coloring agent, the materials chosen should conform with Food and Drug Administration Standards to decrease the possibility of harming the patient 20.

The present invention is directed to a system for intravenous administration of a plurality of medicaments and/or nutrients contained in respective liquid containers. The system includes a plurality of liquid intravenous administration sets. Each administration set includes means for defining a flow path from a point of entry of the flow path adapted to be fluidly connected to a respective liquid container to a point of exit of the flow path adapted to be fluidly connected to a vasopuncture device. The flow path is bound over a portion of its length by a flexible intravenous tube. A plurality of indicia means is provided to designate a respective one of the liquid containers containing one of the medicaments and/or nutrients and is associated with a respected one of the administration sets defining a flow path from the one of the liquid reservoirs.

From the foregoing description, it can be seen that the present invention comprises a system for the intravenous administration of at least two different liquids to a patient. It is appreciated by those skilled in the art that changes could be made to the embodiment described above without departing from the broad inventive concept thereof. It is understood, therefore, that this invention is not limited to the particular embodiment disclosed, but it is intended to cover all modifications which are within the scope and spirit of the invention as defined by the appended claims.

I claim:

1. A system for the intravenous administration of at least two different liquids to a patient, said system comprising:
a first flexible single-walled tube having a first end, a second end and an interior area for administering a first liquid to a patient, said first tube being fabricated of a polymeric material having a coloring agent such that the first tube is of a first translucent color throughout its entirety, said second end of said first tube for receiving insertion means for placing said tube in fluid communication with the patient;

a first container for storing said first liquid in an interior area thereof, said first container being fabricated of a material selected from the group consisting of a polymer or ceramic having a coloring agent such that the first container is of the first translucent color throughout its entirety, said first end of said first tube being in fluid communication with said interior area of said first container;

a second flexible single-walled tube having a first end, a second end and an interior area for administering a second liquid to a patient, said second tube being fabricated of a polymeric material having a coloring agent such that the second tube is of a second translucent color throughout its entirety, said second end of said second tube for receiving insertion means for placing said second tube in fluid communication with the patient;

a second container for storing the second liquid in an interior area thereof, said second container being fabricated of a material selected from the group consisting of a polymer or ceramic having a coloring agent such that the second container is of the second translucent color throughout its entirety, said first end of said second tube being in fluid communication with the interior area of the second container whereby the first and second tubes and the first and second liquids within the first and second tubes can be readily identified by the color of the tubes and containers.

2. The system as recited in claim 1, wherein said first liquid is a light sensitive liquid and the amount of said coloring agent in said polymeric material of said first tube is sufficient to effectively diffuse light passing through the wall of the first tube into the interior area to maintain effective administration of said light sensitive liquid and the amount of coloring agent in said first container material is sufficient to effectively diffuse light passing into the interior area thereof to maintain effective administration of said light sensitive liquid.

3. The system as recited in claim 1, wherein said ceramic is glass.

4. The system as recited in claim 1, further including an injection coupler in fluid communication with said first tube having an insertion portion and a flow through portion, said flow through portion being of the same color as said first tube, said insertion portion being of the same color as said second tube, said insertion portion for receiving the second liquid in said second tube therethrough, to thereby quickly and reliably combine liquids.

5. A system for the intravenous administration of a plurality of different liquids to a patient, said system comprising:

a plurality of flexible single-walled tubes each tube having an interior area for administration of a plurality of different liquids to a patient, each of said tubes being fabricated of a polymeric material, the material used to form each tube having a different coloring agent from the material used to form the other tubes such that each of the tubes is of a different translucent color throughout its entirety, each tube color being associated with a specific liquid;

a plurality of containers for storing the plurality of different liquids, each of said containers being fabricated of a material selected from the group consisting of a polymeric or ceramic having a different coloring agent than the coloring agent of the other containers such that each of the containers is of a different translucent, color throughout its entirety, each such container color being associated with a specific liquid, each of said tubes and said containers of the same color being in fluid communication with each other;

each of said tubes being adapted to receive insertion means for placing said tubes in fluid communication with one or more blood vessels of the patient, whereby the specific type of liquid within each of the tubes and each of the containers can be readily identified by the color of the tubes and containers.

6. A method of administering a plurality of liquids to a patient in need of such administration, said method comprising the steps of:

infusing a plurality of medicaments into one or more blood vessels of the patient, wherein at least two of the liquids flow individually into the patient through an administration system according to claim 1.

* * * * *